(12) United States Patent
Andrelczyk

(10) Patent No.: US 9,383,368 B2
(45) Date of Patent: Jul. 5, 2016

(54) METHODS FOR DETECTING HEPARIN/PLATELET FACTOR 4 ANTIBODIES

(71) Applicant: Akers BioSciences, Inc., Thorofare, NJ (US)

(72) Inventor: Susan Andrelczyk, West Deptford, NJ (US)

(73) Assignee: Akers Biosciences, Inc., Thorofare, NJ (US)

( * ) Notice: Subject to any disclaimer, the term of this patent is extended or adjusted under 35 U.S.C. 154(b) by 0 days.

(21) Appl. No.: 14/275,457

(22) Filed: May 12, 2014

(65) Prior Publication Data

US 2015/0241444 A1 Aug. 27, 2015

Related U.S. Application Data

(62) Division of application No. 11/244,197, filed on Oct. 4, 2005, now abandoned.

(60) Provisional application No. 60/615,622, filed on Oct. 4, 2004.

(51) Int. Cl.
| | |
|---|---|
| *G01N 33/543* | (2006.01) |
| *G01N 33/68* | (2006.01) |
| *B01L 3/00* | (2006.01) |
| *G01N 33/564* | (2006.01) |
| *G01N 33/86* | (2006.01) |

(52) U.S. Cl.
CPC .......... *G01N 33/6863* (2013.01); *B01L 3/5023* (2013.01); *G01N 33/54313* (2013.01); *G01N 33/564* (2013.01); *G01N 33/6893* (2013.01); *G01N 33/86* (2013.01); *B01L 2200/16* (2013.01); *B01L 2300/0681* (2013.01); *B01L 2400/0683* (2013.01); *G01N 2333/522* (2013.01); *G01N 2400/40* (2013.01); *G01N 2800/222* (2013.01)

(58) Field of Classification Search
None
See application file for complete search history.

(56) References Cited

U.S. PATENT DOCUMENTS

| | | | |
|---|---|---|---|
| 4,459,361 A | 7/1984 | Gefter | |
| 4,613,665 A | 9/1986 | Larm | |
| 4,707,471 A | 11/1987 | Larm et al. | |
| 4,717,654 A | 1/1988 | Savoca et al. | |
| 4,795,745 A | 1/1989 | Larm et al. | |
| 4,810,784 A | 3/1989 | Larm | |
| 4,843,550 A | 6/1989 | Kawanabe et al. | |
| 5,049,403 A | 9/1991 | Larm et al. | |
| 5,213,898 A | 5/1993 | Larm et al. | |
| 5,231,035 A | 7/1993 | Akers, Jr. | |
| 5,466,582 A | 11/1995 | Amiral | |
| 5,565,366 A | 10/1996 | Akers, Jr. | |
| 5,618,917 A | 4/1997 | Toback et al. | |
| 5,624,904 A | 4/1997 | Krieger et al. | |
| 5,827,749 A | 10/1998 | Akers, Jr. | |
| 5,972,717 A | 10/1999 | Aster et al. | |
| 5,972,718 A | 10/1999 | Moghaddam et al. | |
| 6,846,638 B2 | 1/2005 | Shipwash | |
| 7,585,641 B2 * | 9/2009 | Bandla et al. | 435/7.8 |
| 2005/0221379 A1 | 10/2005 | Hechinger | |
| 2006/0008854 A1 | 1/2006 | Sabucedo et al. | |
| 2006/0172438 A1 | 8/2006 | Milunic et al. | |

FOREIGN PATENT DOCUMENTS

| | | |
|---|---|---|
| JP | H05-506311 A | 9/1993 |
| WO | 9202823 A1 | 2/1992 |
| WO | 9205440 A1 | 4/1992 |
| WO | 9731259 A1 | 8/1997 |
| WO | 9732211 A1 | 9/1997 |

OTHER PUBLICATIONS

Hui et al., Use of poly(ethylene glycol) to control cell aggregation and fusion, Colloids and Surfaces B: Biointerfaces 14 (1999) 213-222.
Office Action issued Apr. 23, 2008 in U.S. Appl. No. 11/244,198 by Milunic.
Office Action issued Jan. 22, 2009 in U.S. Appl. No. 11/244,197 by Milunic.
Office Action issued Jul. 21, 2009 in U.S. Appl. No. 11/244,197 by Milunic.
Office Action issued Apr. 28, 2010 in U.S. Appl. No. 11/244,197 by Milunic.
Office Action issued Feb. 14, 2011 in U.S. Appl. No. 11/244,197 by Milunic.
Office Action issued Oct. 27, 2011 in U.S. Appl. No. 11/244,197 by Milunic.
Office Action issued Jun. 13, 2013 in U.S. Appl. No. 11/244,197 by Milunic.
English translation of an Office Acton issued Jul. 30, 2013 in JP Application No. 2011-229316.
Office Action issued Feb. 12, 2014 in U.S. Appl. No. 11/244,197 by Milunic.
Office Action issued Jun. 8, 2010 in JP Application No. 2007-534920.
U.S. Appl. No. 60/599,803 by Akers, Jr., filed Aug. 5, 2004.

(Continued)

*Primary Examiner* — Gary W Counts
(74) *Attorney, Agent, or Firm* — Panitch Schwarze Belisario & Nadel LLP

(57) ABSTRACT

Methods for determining the presence of heparin/platelet factor 4 antibodies in a sample suspected to contain heparin/platelet factor 4 antibodies are provided, along with apparatus suitable for performing the methods. The method depends upon a color visualization indicating the presence or absence of heparin/platelet factor 4 antibodies in the sample. Preferred methods comprise contacting the sample with particles being complexed to platelet factor 4 (PF4) and which particle-complexed PF4 reacts specifically with heparin/platelet factor 4 antibodies, passing the sample/particle mixture through a filter, and then analyzing the color of the filtrate. The presence of heparin/platelet factor 4 antibodies in the sample is established where the color of the filtrate is substantially different from the color of the receptor-bearing particles.

15 Claims, 4 Drawing Sheets

(56) References Cited

OTHER PUBLICATIONS

Amiral et al, "Platelet factor 4 complexed to heparin is the target for antibodies generated in heparin-induced thrombocytopenia," Thromb. Haemost., vol. 6, No. 68, pp. 95-96 (1992).
Chong et al, "The clinical usefulness of the platelet aggregation test for the diagnosis of heparin-induced thrombocytopenia," Thromb. Haemost., vol. 69, No. 4, pp. 344-350 (1993).
Collins et al, "Diagnostic testing for heparin-induced thrombocytopenia (HIT): An enhanced plately factor 4 complex enzyme linked immunosorbent (PF4 ELISA)," Blood Suppl. 1, pp. 90:461a (1997).
Greinacher A. et al. "Heparin-associated thrombocytopenia: isolation of the antibody and characterization of a multimolecular PF4-heparin complex as the major antigen." Thromb Haemost. vol. 71 (2): pp. 247-251(1994).
Horsewood P. et al. "The epitope specificity of heparin-induced thrombocytopenia." Br. J. Haematol. vol. 95(1): pp. 161-167 (1996).
Reilly R.F. "The Pathophysiology of immune-mediated heparin-induced throombocytopenia." Semin Dial. vol. 16(1): pp. 54-60 (2003).
Sheridan D. et al. "A diagnostic test for heparin-induced thrombocytopenia." Blood, vol. 67(1): pp. 27-30 (1986).
Tazzari P.L. et al. "Heparin-induced thrombocytopenia: detection of antiheparinIPF4 antibodies by means of heparinIPF4-coated beads and flow cytometry." Tranfus Med. vol. 12(3):pp. 193-198 (2002).
Visentin G.P. et al. "Antibodies associated with heparin-induced thrombocytopenia (HIT) report conformational changes in platelet factor 4 (PF4) induced by linear, polyanionic compounds." Blood (Suppl 1) pp. 90:460a(1997).
Visetin G.P. et al. "Antibodies from patients with heparin-induced thrombocytopenia/thrombosis are specific for platelet factor 4 complexed with heparin or bound to endothelial cells." J Clin Invest. vol. 93(1): pp. 81-88 (1994).
Visentin G.P. et al. "Heparin is not required for detection of antibodies associated with heparin-induced thrombocytopenia/thrombosis." J Lab Clin Med. vol. 138(1): pp. 22-31 (2001).
Amiral, et al., 1995, "Antibodies to Macromolecular Platelet Factor 4-Heparin Complexes in Heparin-induced Thrombocytopenia: a Study of 44 Cases," Thromb Haemost 73:21-28.
Arepally, et al., 1995, "Comparison ofPF4/Heparin ELISA Assay With the .sup. 14 C-Serotonin Release Assay in the Dialmosis of Heparin-induced Thrombocytopenia," COO$! Trans. Med. 104(6):648-654.
Aster, 1989, "The Immunologic Thrombocytopenias," Platelet Immunobiology Molecular and Clinical Aspects 1.B. • Lippincott Company, Philadelphia, PA, pp. 387 and 392.
Aster, 1995, "Heparin-induced Thrombocytopenia and Thrombosis," New Eng. J. Med. 332(20):1374-1376.
Chong, et al., 1993, "The Clinical Usefulness of the Platelet Aggregation Test for the Diagnosis of Heparin-induced Thrombocytopenia," Thromb. Haemost. 69(4):344-350.
Christie, et al., 1982, "Drug-Antibody-Platelet Interaction in Quinine- and Quinidine-induced Thrombocytopenia," J. C/in. Invest. 70:989-998.
Christie, et al., 1985, "Fab-mediated Binding of Drug-dependent Antibodies to Platelets in Quinidine- and Quinineinduced Thrombocytopenia," J. C/in. Invest. 75:310-3 14.
Fukuda, et al., 1989, "Survival of Recombinant Erythropoietin in the Circulation: The Role of Carbohydrates," Blood 73(I):84-89.
Galli, et al., 1994, "Anti-Glycoprotein Ib/IX and IIb/IIIa Antibodies in Patients with Antiphospholipid Antibodies," Thromb Haemost 71(5):571-575.
Godal, 1989, "Heparin-induced Thrombocytopenia," Heparin: Chemical and Biological Properties, Clinical Applications, CRC Press, Inc., Boca Raton, Florida, pp. 533-543.
Greinacher, 1995, "Antigen Generation in Heparin-Associated Thrombocytopenia: The Nonimmunologic Type and the Immunologic Type Are Closely Linked in Their Pathogenesis," Sem. Thromb. Haemost. 21(1):106-116.
Greinacher, et al., 1995, "Characterization of the Structural Requirements for a Carbohydrate Based Anticoagulant with a Reduced Risk of Inducing the Immunological Type of Heparin-associated Thrombocytopenia," Thromb. Haemost.. 74(3):886-892.
Greinacher, et al., 1994, "Laboratory diagnosis of heparin-associated thrombocytopenia and comparison of platelet aggregation test, heparin-induced platelet activation test, and platelet factor 4/heparin enzyme-linked immunosorbent assay," Transfusion 34(5):381-382.
Hoffman, et al., 1983, "A new method for covalent coupling of heparin and other glycosaminoglycans to substances containing primary amino groups," Carbo Res. 117:328-331.
Ihrcke et al., I993, "Role of Heparan Sulfate in Immune System—Blood Vessel Interactions," Immunol. Todav. 14:500-505.
Kelton, 1996, "Heparin-induced Thrombocytopenia: What the Serologists have Taught us," J. Lab. C/in. Med. 128 (4):346-348.
Kelton, et al., 1988, "Heparin-Induced Thrombocytopenia: Laboratory Studies," Blood 72(3):925-930.
Kelton, et al., 1995, "Diagnosis of Heparin-induced Thrombocytopenia," Am. J. C/in. Path. 104(6):611-613.
Kelton, et al., 1994, "Immunoglobin G from Patients with Heparin-induced Thrombocytopenia Binds to a Complex of Heparin and Platelet Factor 4," Blood 83(I 1):3232-3239.
Lafrance, et al., 1995, "Improved Heparin-Agarose: Higher Loading and Greater Stability," in Sigma Com., pp. 2 and 3, 1995 (advertising communication from Sigma Chemical Co.).
Larm, et al., 1977, "Coupling of proteins and other amines to carbohydrate polymers via bromine oxidation and reductive animation," Carbo Res. 58:249-251.
Larm, et al., 1989, "Surface-immobilized heparin," in Heparin: Chemical and Biological Properties; Chemical Aoolications, D. A. Lane, U. Lindahl Eds., CRC Press, Boca Raton, Florida, po. 597-608.
Linhardt, et al., 1992, "Isolation and Characterization of Human Heparin." Biochemistry 31: 12441-12445.
Maccarana, et al., 1993, "Mode of interaction between Platelet Factor 4 and Heparin," Glycobio. 3(3):271-277.
Mayo, et al., 1995, "Heparin Binding to Platelet Factor-4," Biochem. J. 312:357-365.
Morgan et al., 1979, "Complete Covalent Structure of Human Platelet Factor 4," Thromb. Haemost. 42: 1652-1660.
Nadkarni, et al., 1995, "Directional Immobilization of Heparin onto Beaded Supports," Anal. Biochem. 222:59-67.
Sheridan, et al., 1986, "A Diagnostic Test for Heparin-induced Thrombocytopenia," Blood 67(1 ):27-30.
Stuckey, et al., 1992, "A Model of the Platelet Factor 4 Complex with Heparin," Proteins 14:277-287.
Visentin, et al., 1991, "Characteristics of Quinine- and Quinidine-Induced Antibodies Specific for Platelet Glycoproteins IIb and IIIa," Blood 77(12):2668-2676.
Visentin, et al., 1993, "Antibodies Assocaited with Heparin-Induced Thrombocytopenia and Thrombosis (HITP) Recognize Platelet Factor 4 (FR) Bound to Heparin or Endothelial Cell Glycosaminoglycans (GAG)," Blood 82 (Suppl. 1):I63a (abstract No. 634).
Visentin, et al., 1994, "A Prospective Study of the Formation of Antibodies Reactive with Heparin:PF4 Complexes in Patients Treated with Heparin," Abstract, ASH Meeting, Dec. 2-4, 1994.
Visentin, et al., 1994, "Determinants on Heparin:PF4 Complexes Recognized by Antibodies Associated with Heparin-Induced ThrombocytopeniaIThrombosis (HITP)," Blood 4[10] :Suppl. 1.
Zhang, et al., 1994, "Crystal Structure of Recombinant Human Platelet Factor 4," Biochem. 33:836 I-8366.
Akers Laboratories, Inc. HealthTEST© HeparinIPlatelet Factor 4 Antibody Assay. 501(k) Notification. www.fda.gov/cdrhipdf4/k040293.pdf, May 28, 2004.
International Search Report for International Application No. PCT/US2005/036109, Apr. 7, 2006.
Newman et al., Further characterization of antibody and antigen in heparin-induced thrombocytopenia, British Journal of Haematology 1999, 107, pp. 3003-309.

\* cited by examiner

METHODS FOR DETECTING HEPARIN/PLATELET FACTOR 4 ANTIBODIES

CROSS REFERENCE TO RELATED APPLICATIONS

This application is a divisional of U.S. application Ser. No. 11/244,197, filed Oct. 4, 2005, now abandoned, which claimed priority from U.S. Provisional Application No. 60/615,622, filed Oct. 4, 2004, the disclosures of which are incorporated by reference herein in their entireties.

FIELD OF THE INVENTION

The present invention relates to methods and kits useful for detecting heparin-induced thrombocytopenia (HIT) in a subject suspected of having HIT. In particular, the invention relates to methods and kits for the detection of heparin/platelet factor 4 antibodies in a sample by particulate immunofiltration assays, which are faster, simpler, and less expensive to operate than those previously known in the art.

BACKGROUND OF THE INVENTION

Thrombocytopenia is a disorder in which the number of platelets in the blood is abnormally low. Drug-induced immune thrombocytopenia is a condition where the use of certain drugs leads to the formation of antibodies against platelets. These antibodies can cause a decrease in platelet count, resulting in the potential for increased bleeding and decreased ability for clotting. If these antibodies are formed during pregnancy, they may pass from the mother to the fetus.

Heparin is the most widely used intravenous anticoagulant and one of the most widely prescribed drugs in the United States. More than 1 trillion units are administered annually to approximately 12 million patients. Intravenous heparin is commonly used for the prophylaxis and treatment of thromboembolic disease, as well as numerous other applications including certain types of lung and heart disorders, and during or after a variety of surgery including open heart, bypass, dialysis and orthopedic procedures. Heparin is also used for diagnostic and therapeutic interventional radiologic procedures. Due to the widespread use of unfractionated and low molecular weight heparins, heparin-induced thrombocytopenia (HIT) is considered to be the most frequent (and potentially the most devastating) drug-induced thrombocytopenia (Picker S. M. et al. Pathophysiology, epidemiology, diagnosis and treatment of heparin-induced thrombocytopenia (HIT). *Eur J Med Res.* 2004 Apr. 30; 9(4):180-5. Review).

HIT is classified into Type I and Type II, Type I being benign and Type II severe. Type I HIT occurs early after heparin initiation, the platelet levels are reduced only slightly and usually return to normal even when heparin treatment is continued. Thromboembolic complications are rare and Type I HIT is not antibody-mediated.

In contrast, Type II HIT is caused by antibody formation to heparin-platelet factor 4 complexes (Harenberg J. et al. Heparin-induced thrombocytopenia: pathophysiology and new treatment options. *Pathophysiol Haemost Thromb.* 2002 September-December; 32(5-6):289-94. Review). Type II HIT typically develops between 5 and 14 days after heparin therapy is started. The hallmark symptoms of Type II HIT are a drastic fall in platelet count and thrombosis, which can lead to limb gangrene (requiring leg amputation) or even death. Other symptoms of Type II HIT may include cutaneous reactions, from a simple allergic reaction to lesions to necrosis.

Type II HIT occurs in approximately 1-5% of patients treated with heparin (Goor Y. et al. Heparin-induced thrombocytopenia with thrombotic sequelae: a review. *Autoimmun Rev.* 2002 August; 1(4):183-9. Review). More alarmingly, 25-50% of post-cardiac surgery patients develop these heparin-dependent antibodies during the next 5 to 10 days (Warkentin T. E. et al. Heparin-induced thrombocytopenia and cardiac surgery. *Ann Thorac Surg.* 2003 December; 76(6):2121-31. Review). The rate of mortality and amputation in Type II HIT is estimated to be 30% and 20%, respectively (Picker S. M. et al. supra.).

Early diagnosis of HIT is essential to reduce morbidity and mortality. Currently, there are three methods of detecting heparin-induced antibodies: (1) functional tests such as the 14C-serotonin release assay (Sheridan D. et al. A diagnostic test for heparin-induced thrombocytopenia. *Blood.* 1986 January; 67(1): 27-30); (2) platelet aggregation tests (Chong B. H. et al. The clinical usefulness of the platelet aggregation test for the diagnosis of heparin-induced thrombocytopenia. *Thromb Haemost.* 1993 Apr. 1; 69(4): 344-50); and (3) immunoassays such as enzyme-linked immunosorbent assay (ELISA). Although serologic assays to detect and identify platelet-reactive antibodies have progressed from less sensitive and specific Phase I tests (e.g., those that measure platelet functional endpoints) through more sensitive Phase II assays (e.g., those that detect platelet-associated immunoglobulins), to highly specific Phase III assays (e.g., those that detect antibodies bound to alloantigens located on isolated platelet surface glycoproteins), these tests are used primarily as confirmation of HIT after the symptoms are seen in a patient and take many hours to perform. A more efficient, sensitive and specific assay to diagnose HIT remains elusive.

BRIEF SUMMARY OF THE INVENTION

To achieve the aforementioned objectives, the inventors have invented methods and kits for detecting heparin/platelet factor 4 antibodies in a variety of substances. The methods and kits depend upon a color visualization methodology indicating the presence or absence of heparin/platelet factor 4 antibodies. Preferably, the color visualization does not require the use of complicated instrumentation or equipment such that all color changes are readily detected by the naked human eye.

The invention is based, in part, on the inventors' surprising discovery that complexing isolated platelet factor 4 (PF4) to a particle, preferably a spherical particle, induces a conformational change in the PF4 molecule such that it reacts specifically with heparin/platelet factor 4 antibodies (i.e., antibodies that detect PF4 complexed to heparin) in patient samples. The surprising discovery is the basis for methods and kits comprising isolated PF4 complexed to colored particles, preferably spherical particles or beads, in rapid, efficient, sensitive, specific particulate immunofiltration assays to detect HIT.

In certain embodiments, the invention provides methods that use a particulate immunofiltration assay (PIFA®) (Akers Biosciences, Inc., Thorofare, N.J.) to detect heparin/platelet factor 4 antibodies in a liquid sample. The preferred method of the invention comprises incubating the sample with colored, particularly color detectable by the naked eye, particles being complexed to platelet factor 4 (PF4) ("PF4-complexed particles") and which particle-complexed PF4 reacts specifically with heparin/platelet factor 4 antibodies such that the particles have the capacity to form specific aggregates upon contacting heparin/platelet factor 4 antibodies. As used herein, the term "specific aggregates" refer to aggregates that form because of this antibody-antigen interaction. The sample/particles mixture is then passed through a filter having apertures which are larger than the particles but smaller than the specific aggregates, in order to remove any specific and/or non-specific aggregates from the filtrate. The filtrate is then passed through a wicking membrane that is adjacent to the filter, in order to separate unaggregated particles from any non-specifically aggregated particles as well as any remaining specific aggregates, the unaggregated particles being able to migrate horizontally through the wicking membrane at a rate faster than both the non-specifically aggregated particles and specific aggregates. The color of the filtrate is then analyzed, wherein the absence of color suggests the presence of heparin/platelet factor 4 antibodies and the presence of color suggests the absence of heparin/platelet factor 4 antibodies. In one embodiment, the color of the filtrate is analyzed by comparing with a visual standard corresponding to a known concentration of the particles, wherein the presence of heparin/platelet factor 4 antibodies is established where the color of the filtrate is substantially different from the color of the visual standard, and the absence of heparin/platelet factor 4 antibodies is established where the color of the filtrate is substantially similar to the color of the visual standard.

In a preferred embodiment, the particles are spherical, preferably microspheres. In another specific embodiment, the particles are non-spherical.

In one embodiment, after complexing with PF4, the particles are dried and/or sealed in a glass ampoule after being complexed to PF4.

In another embodiment, the particles have a mean diameter from about 0.01 micrometers to about 100 micrometers, preferably about 0.1 micrometers to about 10 micrometers, more preferably about 0.2 micrometers to about 0.6 micrometers, most preferably about 0.3 micrometers.

In one embodiment, the particles are anionic compounds and have negative charges on their surfaces. In preferred embodiments, the particles are made of polyanionic compounds or have polyanionic charges on their surfaces. In a preferred embodiment, the particles comprise latex. In a specific embodiment, the particles comprise latex in the concentration of from about 0.01% w/v to about 2% w/v, preferably from about 0.3% w/v to about 0.4% w/v.

In another preferred embodiment, the particles comprise polystyrene. In a specific embodiment, the particles comprise polystyrene or styrene primary amino latex.

In another preferred embodiment, the particles comprise a metal colloid. In a specific embodiment, the particles comprise gold colloid.

In certain embodiments, the particles are stabilized with a colloidal stabilizer. In a specific embodiment, the colloidal stabilizer comprises sodium tripolyphosphate in the concentration range of from about 0.001% w/v to about 0.1% w/v, preferably from about 0.01% w/v to about 0.1% w/v.

In another specific embodiment, the colloidal stabilizer comprises one or more anionic detergents selected from the group consisting of sodium dodecyl sulphate, sodium laurel sarcosine, polyoxyethylene sorbitan monolaureate, sodium polymetaphosphate, sodium phosphate glass (i.e., sodium hexametaphosphate), sodium pyrophosphate, and other polyphosphate molecules. In preferred embodiments, the one or more anionic detergents are in the concentration range of from about 0.0001% w/v to about 0.1% w/v, preferably from about 0.001% w/v to about 0.01% w/v.

In yet another specific embodiment, the colloidal stabilizer comprises a non-ionic detergent.

In specific embodiments, the PF4 complexed to the particles reacts specifically with heparin/platelet factor 4 antibodies such that the particles have the capacity to form aggregates upon contacting heparin/platelet factor 4 antibodies. The particles are incubated with the sample for a length of time sufficient for aggregates to form, preferably for about 5 minutes. More preferably, a reaction enhancer solution is added to the sample/particles mixture to optimize speed and sensitivity of the aggregation reaction.

In one embodiment, the reaction enhancer solution has a pH of 7.2. In a specific embodiment, the reaction enhancer solution comprises polyethylene glycol, sodium chloride, and glycine. In a more specific embodiment, the reaction enhancer solution comprises polyethylene glycol 8000 in the range of from about 5% w/v to about 15% w/v, preferably from about 8% w/v to about 12% w/v. In another more specific embodiment, the reaction enhancer solution comprises either no sodium chloride (i.e., about 0.0%) or up to about 1% w/v, preferably about 0.1% w/v. In yet another more specific embodiment, the reaction enhancer solution comprises glycine in the range of from about 0.01 molar to about 0.2 molar, preferably from about 0.02 molar to about 0.1 molar.

In one embodiment, the filter comprises a controlled pore membrane. In a specific embodiment, the filter comprises a controlled pore polycarbonate membrane. In preferred embodiments, the filter has apertures which are larger than the particles but smaller than the aggregates. In a specific embodiment, the apertures are from about 5 to about 15 larger than the particles. In another specific embodiment, the apertures are from about 10 to about 12 larger than the particles.

In one embodiment, the filter separates a majority of any specific aggregates from any non-specifically aggregated particles and/or any unaggregated particles. In a specific embodiment, the filter separates about 50%, 60%, 70%, 80%, 90%, 95%, 96%, 97%, 98%, 99%, or all specific aggregates from any non-specifically aggregated particles and/or any unaggregated particles. In a preferred embodiment, the filter separates more than 90% of specific aggregates from any non-specifically aggregated particles and/or any unaggregated particles. The specific aggregates may be separated from the non-specifically aggregated particles and unaggregated particles based on, for example, size and/or weight, and the level of separation can be determined and/or confirmed by separation methods known to one skilled in the art (e.g., mass spectroscopy, chromatography, etc.).

In one embodiment, the wicking membrane comprises a polymeric material. In a specific embodiment, the wicking membrane comprises non-woven fibers of glass or synthetic polymeric material. In a preferred embodiment, the wicking membrane comprises polyester.

In one embodiment, the wicking membrane separates a majority of any unaggregated particles from any non-specifically aggregated particles and/or any aggregates. In a specific embodiment, the wicking membrane separates about 50%, 60%, 70%, 80%, 90%, 95%, 96%, 97%, 98%, 99%, or all unaggregated particles from any non-specifically aggregated particles and/or any specific aggregates. In a preferred embodiment, the wicking membrane separates more than 90% of unaggregated particles from any non-specifically aggregated particles and/or any specific aggregates. The unaggregated aggregates may be separated from the non-specifically aggregated particles and specific aggregates based on, for example, size and/or weight, and the level of separation can be determined and/or confirmed by separation methods known to one skilled in the art (e.g., mass spectroscopy, chromatography, etc.).

In one embodiment, the unaggregated particles migrate horizontally through the wicking membrane at a rate faster than the non-specifically aggregated particles. In a specific embodiment, the unaggregated particles migrate horizontally through the wicking membrane at a rate from about 2 to about 10 times (i.e., 2, 3, 4, 5, 6, 7, 8, 9, and 10) faster than the non-specifically aggregated particles. In a preferred embodiment, the unaggregated particles migrate horizontally through the wicking membrane at a rate greater than 10 times (e.g., greater than 10, 11, 12, 13, 14, 15, 20, 30, 50, 100, etc.) faster than the non-specifically aggregated particles.

In another embodiment, the unaggregated particles migrate horizontally through the wicking membrane at a rate faster than the specific aggregates. In a specific embodiment, the unaggregated particles migrate horizontally through the wicking membrane at a rate from about 2 to about 10 times (i.e., 2, 3, 4, 5, 6, 7, 8, 9, and 10) faster than the specific aggregates. In a preferred embodiment, the unaggregated particles migrate horizontally through the wicking membrane at a rate greater than 10 times (e.g., greater than 10, 11, 12, 13, 14, 15, 20, 30, 50, 100, etc.) faster than the specific aggregates.

In certain embodiments, the color of the filtrate is compared visually, without aid by a machine. In certain other embodiments, the color of the filtrate is compared optically, with aid by a machine. In a specific embodiment, the color of the filtrate is compared, visually or optically, against a standard corresponding to a known concentration of the particles.

In one embodiment, the presence of heparin/platelet factor 4 antibodies is established where the color of the filtrate is substantially different from the color of the particles (e.g., the filtrate lacks color because particles aggregate and are retained). In another embodiment, the absence of heparin/platelet factor 4 antibodies is established where the color of the filtrate is substantially similar to the color of the particles. In certain embodiments, the color of the filtrate and the color of the particles are quantified and compared by optical means, a reflectometer, or other methods well known to one skilled in the art.

In one embodiment, the sample is a liquid sample obtained from a subject. In a specific embodiment, the sample comprises a mammalian bodily fluid. In a preferred embodiment, the sample comprises a human bodily fluid such as blood, serum, plasma or urine. As used herein, a subject is preferably a mammal such as a non-primate (e.g., cows, pigs, horses, cats, dogs, rats, etc.) or a primate (e.g., monkey and human), most preferably a human.

The present invention also provides kits comprising a reaction cell. The kits can also comprise an assay plate suitable for performance of the methods disclosed. The reaction cells comprise PF4-complexed particles. The assay plates comprise a top member having a filter well and an observation well that is at a fixed distance from said filter well, a filter means adjacent the top member and extending across the filter well, a wicking means adjacent and in fluid communication with the filter means and extending the length of the filter well and the observation well, and a bottom adjacent the wicking means.

In certain embodiments, the kits optionally include a blood separator apparatus as described in U.S. Patent Application No. 60/599,803, filed Aug. 5, 2004, which is incorporated herein by reference in its entirety.

In certain embodiments, the reaction cell comprises PF4-complexed particles. In one embodiment, the sample is mixed with the PF4-complexed particles in the reaction cell. In one embodiment, the reaction cell comprises a breakable vessel that contains PF4-complexed particles. In one embodiment, the reaction cell further comprises a kill solution having the capacity to biologically inactivate any infectious agents in the sample.

In certain embodiments, the assay plates comprise a top member, a filter means, a wicking means, and a bottom member. In a specific embodiment, the top member comprises a filter well and an observation well that is at a fixed distance from said filter well. In a specific embodiment, the filter means is adjacent the top member and extending across the filter well. In a specific embodiment, the wicking means is adjacent and in fluid communication with the filter means and extending the length of the filter well and the observation well. In a specific embodiment, the bottom member is adjacent the wicking means. In preferred embodiments, the top member, filter means, wicking means, and bottom member are held in position with an appropriately applied adhesive.

In one embodiment, the top member comprises a material that is substantially impermeable to aqueous solutions such as those associated with the human body. In a preferred embodiment, the top member comprises polystyrene. In certain embodiments, the top member receives the sample/particles mixture.

In one embodiment, the filter means comprises a controlled pore membrane. In a specific embodiment, the filter means comprises a controlled pore polycarbonate membrane. In preferred embodiments, the filter means has apertures which are larger than the particles but smaller than the aggregates. In a specific embodiment, the apertures are from about 5 times to about 15 times larger than the particles. In another specific embodiment, the apertures are from about 10 times to about 12 times larger than the particles. In yet another specific embodiment, the apertures are from about 2 micrometers to about 12 micrometers, preferably about 3 micrometers.

In one embodiment, the filter means separates a majority of any specific aggregates from any non-specifically aggregated particles and/or any unaggregated particles. In specific embodiments, the filter means separates about 50%, 60%, 70%, 80%, 90%, 95%, 96%, 97%, 98%, 99%, or all specific aggregates from any non-specifically aggregated particles and/or any unaggregated particles. In a preferred embodiment, the filter means separates more than 90% of specific aggregates from any non-specifically aggregated particles and/or any unaggregated particles. The specific aggregates may be separated from the non-specifically aggregated particles and unaggregated particles based on, for example, size and/or weight, and the level of separation can be determined and/or confirmed by separation methods known to one skilled in the art (e.g., mass spectroscopy, chromatography, etc.).

In one embodiment, the wicking means comprises a polymeric material. In a specific embodiment, the wicking membrane comprises non-woven fibers of glass or synthetic polymeric material. In a preferred embodiment, the wicking membrane comprises polyester. In preferred embodiments, the wicking means separates a majority of any unaggregated particles from any non-specifically aggregated particles and/or any aggregates. In specific embodiments, the wicking means separates about 50%, 60%, 70%, 80%, 90%, 95%, 96%, 97%, 98%, 99%, or all unaggregated particles from any non-specifically aggregated particles and/or any specific aggregates. In a preferred embodiment, the wicking means separates more than 90% of unaggregated particles from any non-specifically aggregated particles and/or any specific aggregates. Preferably, the unaggregated particles migrate horizontally through the wicking membrane at a rate faster than the non-specifically aggregated particles and specific aggregates. In a specific embodiment, the unaggregated particles migrate horizontally through the wicking membrane at a rate from about 2 to about 10 times (i.e., 2, 3, 4, 5, 6, 7, 8, 9, and 10) faster than the non-specifically aggregated particles or specific aggregates. In a preferred embodiment, the unaggregated particles migrate horizontally through the wicking membrane at a rate greater than 10 times (e.g., greater than 10, 11, 12, 13, 14, 15, 20, 30, 50, 100, etc.) faster than the non-specifically aggregated particles or specific aggregates.

In one embodiment, the bottom member comprises a relatively non-rigid material. In a specific embodiment, the bottom member comprises a vinyl polymer.

In one embodiment, the assay plate further comprises a substrate positioned between the top member and the filter means and extending across the filter well. In a preferred embodiment, the substrate is a glass substrate that contains PF4-complexed particles and one or more reagents that promote the agglutination (i.e., aggregation) reaction.

In one embodiment, the assay plate further comprises a barrier positioned between the wicking means and the bottom member and is as long as the wicking means. In a preferred embodiment, the barrier prevents the wicking means from coming into direct contact with the bottom member.

In one embodiment, an apparatus for detecting heparin/platelet factor 4 antibodies in a fluid sample comprises a tower having at least one foot, a block channel foot, an ampoule support with a slot for holding an ampoule and a reagent well into which a reagent from the ampoule flows following crushing of the ampoule by the tower. The apparatus also comprises a cover with an opening for receiving the tower such that the foot crushes the ampoule in the ampoule support while the block channel foot blocks the flow of fluid flow to the reagent well. Thus, when the tower is withdrawn, the block channel foot is also withdrawn and allows flow of reagent via the channel to the reagent well. A bottom plate holding a test strip is below the reagent well for receiving the reagent onto the test strip. Preferably, the bottom plate couples to the ampoule support, which in-turn holds an ampoule and is covered by the cover. When the tower is depressed into the cover to crush the ampoule the reagent in the ampoule is released while the block channel foot blocks the flow of the first reagent flow to the reagent well via the channel.

Further, another ampoule may be simultaneously be crushed by a second foot or a spur on the block channel foot to allow mixing of two or more reagents prior to flowing on to the reagent well via the channel. Preferably, the spur is adjacent to the block channel foot and the ampoule support comprises the channel connected to the reagent well.

Preferably, the bottom plate, the test trip, the ampoule support, and the cover are engaged to form a test device operable by depressing and withdrawing the tower.

The many advantages and details of the invention are described further by the following illustrative figures and the detailed description.

BRIEF DESCRIPTION OF THE DRAWINGS

FIG. 1 is a top plan view of an assay plate useful according to the preferred methods and kits of the of the present invention;

FIG. 2 is an expanded sectional view of an assay plate useful according to the preferred methods and kits of the of the present invention;

FIG. 3 is an expanded sectional view of a preferred assay plate useful according to the preferred methods and kits of the of the present invention having a barrier between the wicking means and the bottom member;

FIG. 4 is an expanded sectional view of an assay plate useful according to the preferred methods and kits of the present invention having a substrate beneath the filter well;

FIG. 5 is a perspective view of a reaction cell useful according to the preferred kits of the present invention;

FIG. 6 is a perspective view of a reaction cell useful according to the preferred kits of the present invention comprising "kill" solution in a compartment;

FIG. 7 is a perspective view of a reaction cell useful according to the preferred kits of the present invention comprising "kill" solution in a breakable vessel;

DETAILED DESCRIPTION OF THE INVENTION

Figure 1:
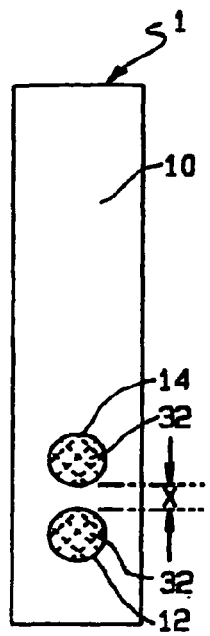
FIGS. 1-7 are taken from U.S. Pat. No. 5,565,366, which is incorporated herein by reference in its entirety.
Figure 2:
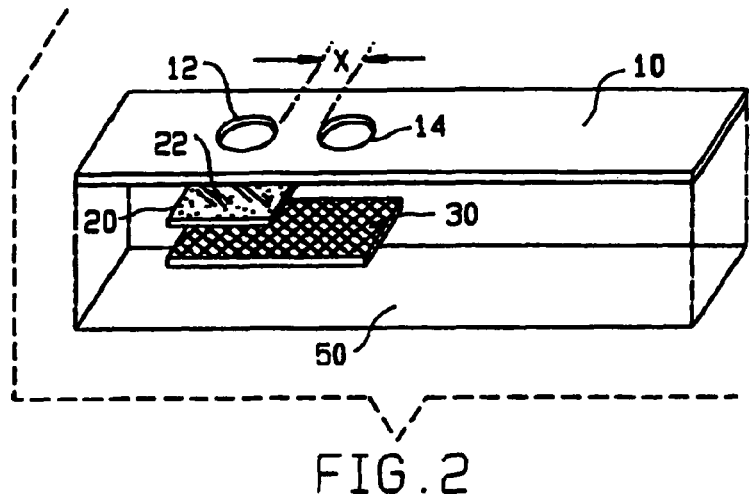
Figure 3:
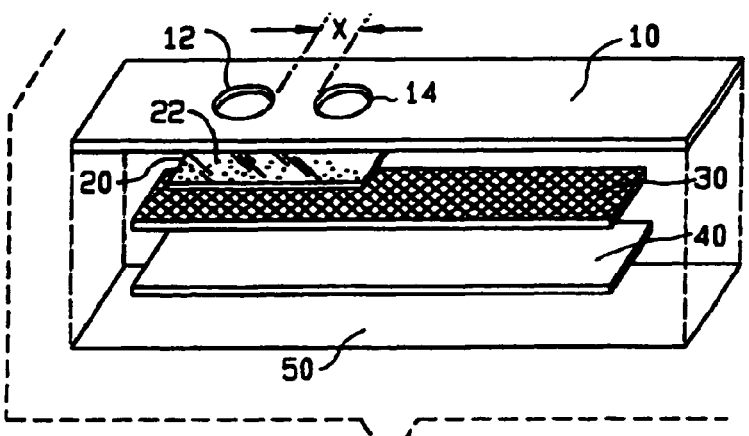

Type II HIT is mediated by an antibody that recognizes an epitope on the platelet protein designated "platelet factor 4" (PF4) that is created when PF4 is complexed to heparin (Horsewood P. et al. The epitope specificity of heparin-induced thrombocytopenia. Br J Haematol. 1996 October; 95(1): 161-7). When heparin binds to PF4, a conformational change in the PF4 molecule occurs and as a result, exposes neo-epitopes that act as immunogens (Reilly R. F. The pathophysiology of immune-mediated heparin-induced thrombocytopenia. Semin Dial. 2003 January-February; 16(1):54-60. Review). Many polyanionic compounds other than heparin can form complexes with PF4 and cause similar conformational change in the molecule (Visentin G. P. et al. Heparin is not required for detection of antibodies associated with heparin-induced thrombocytopenia/thrombosis. J Lab Clin Med. 2001 July; 138(1):22-31).

The invention is based, in part, on inventors' surprising discovery that complexing isolated platelet factor 4 (PF4) to a particle, preferably a spherical particle, more preferably a polyanionic particle (e.g., polystyrene), induces a conformational change in the PF4 molecule such that it reacts specifically with heparin/platelet factor 4 antibodies in patient samples. The surprising discovery is the basis for methods and kits comprising isolated PF4 complexed to colored particles, preferably spherical particles or beads, in rapid, efficient, sensitive, specific particulate immunofiltration assays to detect HIT.

The methods of the invention comprise incubating a sample with particles complexed to platelet factor 4 (PF4) ("PF4-complexed particles"), passing the sample/particles mixture through a filter, and analyzing the color of the filtrate. The kits of the invention comprise a reaction cell for mixing and/or incubating the PF4-complexed particles with the sample. The kits also include an assay plate for filtering and analyzing the sample/particles mixture.

The invention further encompasses using the methods and kits described above for detecting heparin-induced thrombocytopenia (HIT) in a subject suspected of having HIT. The methods and kits can be used in a variety of settings, for example, hospitals, clinics, physician's offices, clinical laboratories, etc.

For clarity of disclosure, and not by way of limitation, the detailed description of the invention is divided into the subsections which follow.

5.1 Particulate Immunofiltration Assay

The particulate immunofiltration assay (PIFA®) (Akers Biosciences, Inc., Thorofare, N.J.) is a system that offers significant advantages in terms of accuracy, ease of use, and rapidity of results. Its principles are based on the selective filtration of particles in response to antibody/antigen binding. Dyed particles coated with antigen or antibody provide the visual signal for the results of the assay: the presence of a corresponding antibody or antigen in the test sample will result in the formation of a matrix of aggregated particles. The ability of matrixed (aggregated) or non-matrixed (unaggregated) particles to move through a filter medium is the measure of the positive or negative reactivity of the test sample.

In practice, the technology involves combining a test sample (e.g., blood, serum, plasma, urine, or saliva) with a reagent, which consists of particles coated with antigen or antibody. During a period of incubation, the reagent is allowed to react with the test sample. Test samples containing corresponding antigens or antibodies (positive samples) will cause the particles to form a matrix (i.e., aggregates); test samples without these substances (negative samples) will leave the particles unaggregated. Once the reagent has reacted with the sample, the mixture is introduced into a device designed to separate aggregated particles from non-specifically aggregated particles (i.e., those particles that form a matrix with each other, or another substance, but not with the corresponding antigens or antibodies) and/or unaggregated particles. This device is a composite of several membranes laminated together, combining controlled pore and liquid flow dynamic properties. By careful control of pore size and density, and liquid flow through a fibrous meshwork, aggregated particles can be efficiently filtered and separated from the rest of the reaction mixture and prevented from entering the inner layers of the device. Conversely, unaggregated particles can penetrate the controlled pore membranes and migrate through the inner membrane layers.

Thus, a positive sample produces aggregated particles that are filtered by the controlled pore membranes; no particles, and hence no color, are able to migrate into successive membrane layers. In this case color is only visible in a first viewing window of the device (see, e.g., (14) of FIG. 1). Conversely, a negative sample does not produce aggregated particles; the dyed unaggregated particles pass through the controlled pore membrane and into successive membrane layers, where they become visible through a second viewing window in the device.

Specific embodiments of PIFA® technology and related kits are described in fuller detail in U.S. Pat. Nos. 5,231,035; 5,565,366; and 5,827,749, all of which are incorporated by reference herein in their entireties.

Specifically, the present invention encompasses the use of PIFA® technology to detect heparin/platelet factor 4 antibodies in a variety of substances. The substance may be of a biological source or a non-biological source exposed to biological material. The preferred methods of the invention comprise incubating the sample with particles being complexed with platelet factor 4 ("PF4-complexed particles"). Once complexed with the particles, the PF4 reacts specifically with heparin/platelet factor 4 antibodies such that the PF4-complexed particles have the capacity to form specific aggregates upon contacting heparin/platelet factor 4 antibodies. The sample/particles mixture is then passed through a filter having apertures which are larger than the particles but smaller than the specific aggregates, in order to remove any specific aggregates from the filtrate. The filtrate is then passed through a wicking membrane that is adjacent to the filter, in order to separate any unaggregated particles from any non-specifically aggregated particles as well as any remaining specific aggregates. The unaggregated particles migrate horizontally through the wicking membrane at a rate faster than both the non-specifically aggregated particles and specific aggregates.

After filtration through the filter and wicking membrane, the filter is analyzed for color changes, preferably, by comparing with a visual standard corresponding to a known concentration of the particles. The presence of heparin/platelet factor 4 antibodies is established where the color of the filtrate is substantially different from the color of the particles; the absence of heparin/platelet factor 4 antibodies is established where the color of the filtrate is substantially similar to the color of the particles.

The particles may be of any lattices which are known or believed to be employable for latex agglutination, such as exemplified by the homopolymers and copolymers produced from styrene or its derivatives such as methylstyrene, ethylstyrene, and chlorostyrene, olefins such as ethylene and propylene, acrylic acid or its esters such as methyl acrylate and ethyl acrylate, methacrylic acid or its derivatives such as ethyl methacrylate, acrylonitrile, and acrylamide, dienes such as butadiene, chloroprene, and isoprene, vinyl chloride, vinylidine chloride, and vinyl acetate. The lattices of homopolymers or copolymers made of styrene, chlorostyrene, acrylic acid, vinyl toluene, methyl methacrylate are advantageously used.

Preferably, the particles the particles are made up of polyanionic compounds. In specific embodiments, the particles comprise polyanionic compounds in the concentration of about 0.001% w/v, about 0.005% w/v, about 0.01% w/v, about 0.05% w/v, about 0.1% w/v, about 0.2% w/v, about 0.3% w/v, about 0.4% w/v, about 0.5% w/v, about 0.6% w/v, about 0.7% w/v, about 0.8% w/v, about 0.9% w/v, about 1.0% w/v, about 1.1% w/v, about 1.2% w/v, about 1.3% w/v, about 1.4% w/v, about 1.5% w/v, about 1.6% w/v about 1.7% w/v, about 1.8% w/v, about 1.9% w/v, about 2.0% w/v, about 2.1% w/v, about 2.2% w/v, about 2.3% w/v, about 2.4% w/v, about 2.5% w/v, about 2.6% w/v, about 2.7% w/v, about 2.8% w/v, about 2.9% w/v, about 3.0% w/v, about 5.0% w/v, about 10% w/v, or more. Preferably, the particles comprise polyanionic compounds in the concentration of from about 0.01% w/v to about 2% w/v, more preferably from about 0.3% w/v to about 0.4% w/v.

In a preferred embodiment, the particles comprise latex. Other useful particles comprise polystyrene, preferably carboxylated polystyrene, with or without reactive groups to facilitate reaction with the receptor, such as amino groups, thiol groups, carboxyl groups or other reactive groups. Butadiene/styrene copolymers such as carboxylated styrene butadiene or acrylonitrile butadiene styrene are also useful. In another preferred embodiment, the particles comprise polystyrene or styrene primary amino latex.

Inorganic particles, such as silicas, clay, carbons such as activated charcoal, and other materials on which the heparin/platelet factor 4 antibodies can be complexed can be used in the present invention.

In another preferred embodiment, the particles comprise metal colloid such as gold colloid. In a specific embodiment, the metal colloid is charged.

In certain embodiments, the particles are stabilized with a colloidal stabilizer. In specific embodiments, the colloidal stabilizer comprises sodium tripolyphosphate in the concentration of about 0.001% w/v, about 0.005% w/v, about 0.01% w/v, about 0.05% w/v, about 0.1% w/v, about 0.2% w/v, about 0.3% w/v, about 0.4% w/v, about 0.5% w/v, about 0.6% w/v, about 0.7% w/v, about 0.8% w/v, about 0.9% w/v, about 1.0% w/v, about 1.1% w/v, about 1.2% w/v, about 1.3% w/v, about 1.4% w/v, about 1.5% w/v, about 1.6% w/v about 1.7% w/v, about 1.8% w/v, about 1.9% w/v, about 2.0% w/v, about 2.1% w/v, about 2.2% w/v, about 2.3% w/v, about 2.4% w/v, about 2.5% w/v, about 2.6% w/v, about 2.7% w/v, about 2.8% w/v, about 2.9% w/v, about 3.0% w/v, about 5.0% w/v, about 10% w/v, or more. Preferably, the colloidal stabilizer comprises sodium tripolyphosphate in the concentration of from about 0.001% w/v to about 0.1% w/v, more preferably from about 0.01% w/v to about 0.1% w/v.

In another specific embodiment, the colloidal stabilizer comprises one or more anionic detergents selected from the group consisting of sodium dodecyl sulphate, sodium laurel sarcosine, polyoxyethylene sorbitan monolaureate, sodium polymetaphosphate, sodium phosphate glass (i.e., sodium hexametaphosphate), sodium pyrophosphate, and other polyphosphate molecules. In specific embodiments, the colloidal stabilizer comprises the anionic detergents in the concentration of about 0.0001% w/v, about 00.001% w/v, about 0.005% w/v, about 0.01% w/v, about 0.05% w/v, about 0.1% w/v, about 0.2% w/v, about 0.3% w/v, about 0.4% w/v, about 0.5% w/v, about 0.6% w/v, about 0.7% w/v, about 0.8% w/v, about 0.9% w/v, about 1.0% w/v, about 1.1% w/v, about 1.2% w/v, about 1.3% w/v, about 1.4% w/v, about 1.5% w/v, about 1.6% w/v about 1.7% w/v, about 1.8% w/v, about 1.9% w/v, about 2.0% w/v, about 2.1% w/v, about 2.2% w/v, about 2.3% w/v, about 2.4% w/v, about 2.5% w/v, about 2.6% w/v, about 2.7% w/v, about 2.8% w/v, about 2.9% w/v, about 3.0% w/v, about 5.0% w/v, about 10% w/v, or more. Preferably, the colloidal stabilizer comprises the anionic detergents in the concentration of from about 0.0001% w/v to about 0.1% w/v, more preferably from about 0.001% w/v to about 0.01% w/v.

In certain other embodiments, the colloidal stabilizer comprises a non-ionic detergent. Examples of non-ionic detergents include, but are not limited to, Triton® X-100 (alkylaryl polyether alcohol or octyl phenol ethoxylate), Triton® X-114 (octylphenol-polyethylene glycol ether), octylthioglucoside, Nonidet® P-40 ([octylphenoxy]polyethoxyethanol), and N-octyl-BD-glucopyranoside.

In one specific preferred embodiment, the particles are spherical, preferably microspheres. In another specific embodiment, the particles are non-spherical.

It is important that the particles are approximately the same diameter, so that they will easily pass through the same size filter aperture. In specific embodiments, the particles have mean diameters of about 0.0001 micrometers, about 0.001 micrometers, about 0.01 micrometers, about 0.05 micrometers, about 0.1 micrometers, about 0.2 micrometers, about 0.3 micrometers, about 0.4 micrometers, about 0.5 micrometers, about 0.6 micrometers, about 0.7 micrometers, about 0.8 micrometers, about 0.9 micrometers, about 1.0 micrometers, about 2.0 micrometers, about 3.0 micrometers, about 4.0 micrometers, about 5.0 micrometers, about 10 micrometers, about 20 micrometers, about 30 micrometers, about 40 micrometers, about 50 micrometers, about 100 micrometers, about 200 micrometers, about 300 micrometers, about 400 micrometers, about 500 micrometers, about 1,000 micrometers, or larger.

In preferred embodiments, the particles have mean diameters of about 0.01 micrometers to about 100 micrometers, preferably about 0.01 micrometers to about 10 micrometers, and more preferably about 0.2 micrometers to about 0.6 micrometers. Most preferably, the mean diameter of the particles is about 0.3 micrometers and the diameters of the particles do not vary from the mean by more than 30%, preferably not by more than 15%, 10%, or 5%.

The particles preferably have a visually recognizable color produced by the addition of dyes, pigments, or coatings. For example, the preparation of dyed polyacrylamide particles is disclosed in U.S. Pat. No. 4,108,974 in the names of Wegfahrt et al., which is incorporated herein by reference. It is preferred that the color be relatively dark, preferably black or dark blue. Preferred particles are the small, uniform diameter colored polystyrene latex spheres available in a variety of diameters from Bangs Laboratories (Carmel, Ind.) and Seradyn, Inc. (Indianapolis, Ind.).

The complexation of particles with platelet factor 4 to expose neo-epitopes that react specifically with heparin/platelet factor 4 antibodies can be effected by any method known in the art for complexing proteins to particles. The treatment conditions will understandably vary to some degree depending upon the physicochemical properties of the selected particles. In a specific embodiment, PF4 can be bound to particles by adsorption, a process which is mediated by hydrophobic and ionic interactions between PF4 and the surface of the particles. In accordance with preferred embodiments, PF4 is covalently bound to the particles. In a specific embodiment, PF4 can be covalently bound to carboxylate-modified particles in the presence of, for example, water-soluble carbodiimide 1-ethyl-3-(3-dimethylaminopropyl)-carbodiimide (EDAC).

While PF4 can also be chemically bonded to the particles, the particles may alternatively be coated with a substance to which PF4 will adhere, so long as the coating does not interfere with the binding between PF4 and the heparin/platelet factor 4 antibodies. The amounts of immobilized PF4 and particles are preferably adjusted so that each of the PF4-complexed particles will aggregate with one or more of the heparin/platelet factor 4 antibodies when mixed together for a reasonable time.

In specific embodiments, the PF4 complexed to the particles reacts specifically with heparin/platelet factor 4 antibodies such that the particles have the capacity to form aggregates upon contacting heparin/platelet factor 4 antibodies. The PF4-complexed particles are incubated with the sample for a length of time sufficient for aggregates to form. In certain embodiments, the PF4-complexed particles are incubated with the sample for at least 30 seconds, at least 1 minute, at least 2 minutes, at least 3 minutes, at least 4 minutes, at least 5 minutes, at least 10 minutes, at least 15 minutes, at least 20 minutes, at least 30 minutes or longer for aggregates to form. In certain embodiments, the PF4-complexed particles are incubated with the sample for no longer than 30 minutes, no longer than 20 minutes, no longer than 15 minutes, no longer than 10 minutes, no longer than 5 minutes, no longer than 4 minutes, no longer than 3 minutes, no longer than 2 minutes, no longer than 1 minute, no longer than 30 seconds or less for aggregates to form. In a preferred embodiment, the PF4-complexed particles are incubated with the sample for about 30 seconds to about 5 minutes. More preferably, a reaction enhancer solution is added to the sample/particles mixture to optimize speed and sensitivity of the aggregation reaction. In one embodiment, the particles are dried and/or sealed in a glass ampoule after being complexed to PF4.

In one embodiment, the sample is a liquid sample obtained from a subject. As used herein, a subject is preferably a mammal such as a non-primate (e.g., cows, pigs, horses, cats, dogs, rats, etc.) or a primate (e.g., monkey and human), most preferably a human. In a specific embodiment, the sample comprises a mammalian bodily fluid. Preferably, the sample comprises a human bodily fluid such as blood, serum, plasma, or urine.

The sample of interest and the PF4-complexed particles may be contacted in a number of ways. In a preferred method, the sample is mixed with a solution that contains the PF4-complexed particles and other reagents helpful to promote the aggregation reaction, forming a test mixture. An interval of time is permitted to pass which is sufficient for aggregation to occur or for aggregates to otherwise form. Alternatively, the sample can be passed through a substrate such as a glass membrane which contains the particles and other reagents (e.g., polyethylene glycol 8000 and dextran 10,000 MW) helpful to promote the aggregation reaction. Where the sample contains ligand, aggregates and other moieties will be released from the substrate. The released aggregates and other moieties also constitute test mixtures according to this invention.

In certain embodiments, a reaction enhancer solution is added to the sample/particles mixture to promote the aggregation reaction. In one embodiment, the reaction enhancer solution has a pH of 7.2. In a specific embodiment, the reaction enhancer solution comprises polyethylene glycol, sodium chloride, and glycine. In a more specific embodiment, the reaction enhancer solution comprises polyethylene glycol 8000 in the range of from about 5% w/v to about 15% w/v, preferably from about 8% w/v to about 12% w/v. In another more specific embodiment, the reaction enhancer solution comprises either no sodium chloride (i.e., about 0.0%) or up to about 1% w/v, preferably about 0.1% w/v. In yet another more specific embodiment, the reaction enhancer solution comprises glycine in the range of from about 0.01 molar to about 0.2 molar, preferably from about 0.02 molar to about 0.1 molar.

The test mixture is then exposed to a filter having apertures which are larger than the particles but generally smaller than the clumps of ligand/particle aggregates which might have formed. In one embodiment, the filter comprises a controlled pore membrane. In a specific embodiment, the filter comprises a controlled pore polycarbonate membrane.

The filter should have a defined pore size which is about 5 to about 15 times larger than the latex particle diameter, preferably about 10 to about 12 times larger, more preferably about 3 micrometers in diameter. It will be appreciated that there may be some small variance in the diameters of the pores. Preferably, the pore diameters will not vary from the nominal diameter by more than 30%, preferably not by more than 15%, 10%, or 5%.

The pore size of the filter is chosen to retain heparin/platelet factor 4 antibodies/particle aggregates yet permit the passage of any relatively small aggregates which may be formed by non-specific aggregation. It will be appreciated that non-specific aggregation is the aggregation of particles in the absence of heparin/platelet factor 4 antibodies. The sensitivity of the assay should be adjusted to produce aggregates larger than the pore size, roughly 10 to 15 particles in diameter. Preferably, the filter will be an absolute channel membrane having pores of controlled diameter.

The filter separates a majority of any specific aggregates from any non-specifically aggregated particles and/or any unaggregated particles. In certain embodiments, the filter separates about 50%, 60%, 70%, 80%, 90%, 95%, 96%, 97%, 98%, 99%, or all specific aggregates from any non-specifically aggregated particles and/or any unaggregated particles. In a preferred embodiment, the filter separates more than 90% of specific aggregates from any non-specifically aggregated particles and/or any unaggregated particles. The specific aggregates may be separated from the non-specifically aggregated particles and unaggregated particles based on, for example, size and/or weight, and the level of separation can be determined and/or confirmed by separation methods known to one skilled in the art (e.g., mass spectroscopy, chromatography, etc.).

Preferred controlled pore membranes are which comprise polycarbonate, such as those commercially available from the Poretics Corporation (Livermore, Calif.).

After passing through the filter, the filtrate is passed through a wicking membrane for further separation. In one embodiment, the wicking membrane comprises a polymeric material. In a specific embodiment, the wicking membrane comprises non-woven fibers of glass or synthetic polymeric material. In a preferred embodiment, the wicking membrane comprises polyester.

The wicking membrane separates a majority of any unaggregated particles from any non-specifically aggregated particles and/or any specific aggregates. In certain embodiments, the wicking membrane separates about 50%, 60%, 70%, 80%, 90%, 95%, 96%, 97%, 98%, 99%, or all unaggregated particles from any non-specifically aggregated particles and/or any specific aggregates. In a specific embodiment, the wicking membrane separates more than 90% of unaggregated particles from any non-specifically aggregated particles and/or any specific aggregates. The unaggregated aggregates may be separated from the non-specifically aggregated particles and specific aggregates based on, for example, size and/or weight, and the level of separation can be determined and/or confirmed by separation methods known to one skilled in the art (e.g., mass spectroscopy, chromatography, etc.).

The unaggregated particles migrate faster through the wicking membrane than non-specifically aggregated particles, and the non-specifically aggregated particles migrate faster through the wicking membrane than the specific aggregates. In one embodiment, the unaggregated particles migrate horizontally through the wicking membrane at a rate faster than the specific aggregates. In a specific embodiment, the unaggregated particles migrate horizontally through the wicking membrane at a rate 1,000 times, 500 times, 100 times, 50 times, 30 times, 20 times, 15 times, 10 times, 5 times, 4 times, 3 times, 2 times faster than the non-specifically aggregated particles. In another specific embodiment, the unaggregated particles migrate horizontally through the wicking membrane at a rate 1,000 times, 500 times, 100 times, 50 times, 30 times, 20 times, 15 times, 10 times, 5 times, 4 times, 3 times, 2 times faster than the specific aggregates. In yet another specific embodiment, the non-specifically aggregated particles migrate horizontally through the wicking membrane at a rate 1,000 times, 500 times, 100 times, 50 times, 30 times, 20 times, 15 times, 10 times, 5 times, 4 times, 3 times, 2 times faster than the specific aggregates.

Once the mixture is filtered, the filtrate produced thereby is analyzed for the presence of particles which are unaggregated. While it will be appreciated that such analysis may be performed by any of the appropriate physical and/or chemical methods known in the art, such as centrifugation or particle counting, analysis of the filtrate is preferably performed by visually inspecting the filtrate to determine the presence therein of a recognizable color corresponding to the particles. Thus, where the proportions of particles and heparin/platelet factor 4 antibodies have been carefully selected, a qualitative system is established wherein the presence in the filtrate of a color corresponding to the particles indicates the absence of heparin/platelet factor 4 antibodies in the sample, and the absence of such color in the filtrate indicates the presence of heparin/platelet factor 4 antibodies in the sample. It is, of course, also possible to determine the quantity of heparin/platelet factor 4 antibodies present in a sample in accordance with the present invention. A suitable quantitative system may be established by comparing the filtrate with one or more visual standards corresponding to known concentrations of colored particles in the filtrate. Such visual standards will be prepared from samples having known concentrations of heparin/platelet factor 4 antibodies.

In certain other embodiments, the color of the filtrate is compared optically, and the amount of heparin/platelet factor 4 antibodies in the filtrate is determined by instruments known to one skilled in the art.

5.2 Kits

The present invention further provides kits suitable for implementing the described methods. In general, such kits comprise: a reaction cell comprising isolated PF4 complexed to particles or beads. The kits additionally contain components such as an assay plate suitable for performance of the filter method and analysis method discussed above.

In a preferred embodiment, the kit comprises two components: a container, such as a plastic pipette, containing the reagents. The reagents are contained in crushable ampoules sealed inside the pipette and comprise PF4-coated particles and other agents helpful to promote rapid antigen/antibody binding.

In one embodiment, the reaction cell comprises a breakable vessel that contains PF4-complexed particles. Optionally, the reaction cell comprises a solution that enhances the aggregation reaction. Optionally, the reaction cell comprises a solution that biologically inactivates any infectious agents in the sample.

The reaction cells can be used for mixing and/or incubating a sample with PF4-complexed particles.

Assay plates according to this invention comprise a top member, a filter means, a wicking means, and a bottom member. In a specific embodiment, the top member comprises a filter well and an observation well that is at a fixed distance from said filter well. In a specific embodiment, the filter means is adjacent the top member and extending across the filter well. In a specific embodiment, the wicking means is adjacent and in fluid communication with the filter means and extending the length of the filter well and the observation well. In a specific embodiment, the bottom member is adjacent the wicking means. In preferred embodiments, the top member, filter means, wicking means, and bottom member are held in position with an appropriately applied adhesive.

In one embodiment, the top member comprises a material that is substantially impermeable to aqueous solutions such as those associated with the human body. In a preferred embodiment, the top member comprises polystyrene. In certain embodiments, the top member receives the sample/particles mixture.

In one embodiment, the filter means comprises a controlled pore membrane. In a specific embodiment, the filter means comprises a controlled pore polycarbonate membrane. In preferred embodiments, the filter means has apertures which are larger than the particles but smaller than the aggregates.

In certain embodiments, the filter means has apertures which are 2 times, 3 times, 4 times, 5 times, 6 times, 7 times, 8 times, 9 times, 10 times, 11 times, 12 times, 13 times, 14 times, 15 times, 20 times, 30 times, 50 times, 100 times, or larger than the particles but smaller than the aggregates. In a specific embodiment, the apertures are from about 5 to about 15 larger than the particles. In another specific embodiment, the apertures are from about 10 to about 12 larger than the particles. In yet another specific embodiment, the apertures are from about 2 micrometers to about 12 micrometers, preferably about 3 micrometers.

The filter means is capable of separating a majority of any specific aggregates from any non-specifically aggregated particles and/or any unaggregated particles. In certain embodiments, the filter means separates about 50%, 60%, 70%, 80%, 90%, 95%, 96%, 97%, 98%, 99%, or all specific aggregates from any non-specifically aggregated particles and/or any unaggregated particles. In a more preferred embodiment, the filter means separates more than 90% of specific aggregates from any non-specifically aggregated particles and/or any unaggregated particles.

In one embodiment, the wicking means comprises a polymeric material. In a specific embodiment, the wicking membrane comprises non-woven fibers of glass or synthetic polymeric material. In a preferred embodiment, the wicking membrane comprises polyester. In preferred embodiments, the wicking means separates a majority of any unaggregated particles from any non-specifically aggregated particles and/or any specific aggregates. In a specific embodiment, the wicking means separates more than 90% of any unaggregated particles from any non-specifically aggregated particles and/or any specific aggregates.

In one embodiment, the bottom member comprises a relatively non-rigid material. In a specific embodiment, the bottom member comprises a vinyl polymer.

In one embodiment, the assay plate further comprises a substrate positioned between the top member and the filter means and extending across the filter well. In a preferred embodiment, the substrate is a glass substrate that contains PF4-complexed particles and one or more reagents that promote the aggregation reaction.

In one embodiment, the assay plate further comprises a barrier positioned between the wicking means and the bottom member and is as long as the wicking means. In a preferred embodiment, the barrier prevents the wicking means from coming into direct contact with the bottom member.

Examples of preferred assay plate (1) that can be used in the kits of the present invention are shown in FIGS. 1 through 7, which are taken from U.S. Pat. No. 5,565,366, which is incorporated herein by reference in its entirety. The assay plates useful for the methods and kits of this invention generally comprise: a substantially flat top member (10) of predetermined dimensions having a filter well (12) and an observation well (14); filter means (20) adjacent the top member and extending across the filter well; wicking means (30) adjacent the filter means and extending the length and width of the filter well and the observation well; and a substantially flat bottom member (50) having the approximate dimensions of the top member, adjacent the wicking means. It will be appreciated that analysis means comprises elements of the assay plates other than the filter means.

The top member preferably comprises a material which is substantially impermeable to aqueous solutions such as those associated with the human body. The top member preferably is cut or stamped from a rigid material and, thus, is able to impart some degree of support to the assay plate. It is preferred that the top member comprise polystyrene and have a length of about 100 millimeters, a width of about 20 millimeters, and a thickness of about 1.0 millimeters.

The top member should be cut, stamped, or otherwise fabricated to have a filter well (12) and an observation well (14) extending though the entire thickness of the top member. Preferably, the filter well and the observation well are circular, but other shapes are possible. It is also preferred that the filter well and the observation well be a predetermined distance (X) from one another. Since there exists the possibility that some aggregates might not form clumps of sufficient diameter to be retained by the filter, the predetermined distance (X) is selected such that any aggregates which pass through the filter do not reach the observation window. Thus, the predetermined distance (X) will vary with the specific particle and wicking means employed. It will generally be the case that the distance (X) varies in an inverse fashion with the capacity of the wicking means to retain aggregates.

The filter means (20) is preferably a filter as described above having apertures (22) which are larger than the particles but generally smaller than the clumps of aggregates. It is preferred that the filter means be a controlled pore polycarbonate membrane. While the filter means need only extend across the filter well, where the filter means is transparent or nearly transparent, such as where the filter means is a controlled pore polycarbonate membrane, the filter means preferably also extends across the observation well, as in FIG. 3.

Adjacent the filter means is the wicking means (30). The wicking means is preferably positioned in close physical contact with the filter means such that filtrate flows vertically into the wicking means and migrates horizontally from a position beneath the filter well to a position beneath the observation well. While the filter means need only extend the length of the filter well and the observation well, the wicking means is preferably somewhat longer, as in FIG. 3. The filter means and the wicking means are preferably attached to one another with a porous adhesive, such as the adhesive available from Adhesive Research Company (Glen Rock, Pa.) under the trade name ARcare Porous. It is preferred that the wicking means comprise non-woven fibers of glass or natural or synthetic polymeric materials, preferably polyester. The composition and arrangement of the fibers in the wicking means are selected such that the aggregates and the particles migrate thereon at different rates. Preferably the particles migrate faster. It is also preferred that the wicking means have an embossed or otherwise formed visually recognizable pattern, such as a cross-hatch pattern (32), to facilitate the visual detection of color at the observation well.

The bottom member (50) is adjacent the wicking means and preferably comprises a material which is substantially impermeable to aqueous solutions. The bottom member preferably is cut or stamped to have the approximate width and length of the top member. The top member and/or the bottom member should serve to support the assay plate. Thus, where the top member provides adequate support, the bottom member may comprise a relatively non-rigid material, such as a vinyl polymer. The bottom member is preferably physically attached to the other components of the assay plate with an adhesive. Since many suitable adhesives impair the wicking properties of the wicking means, preferred assay plates have a barrier (40) such as a thin polyethylene film at least as long as the wicking means and positioned between the wicking means and the adhesive-bearing bottom member.

Figure 4:
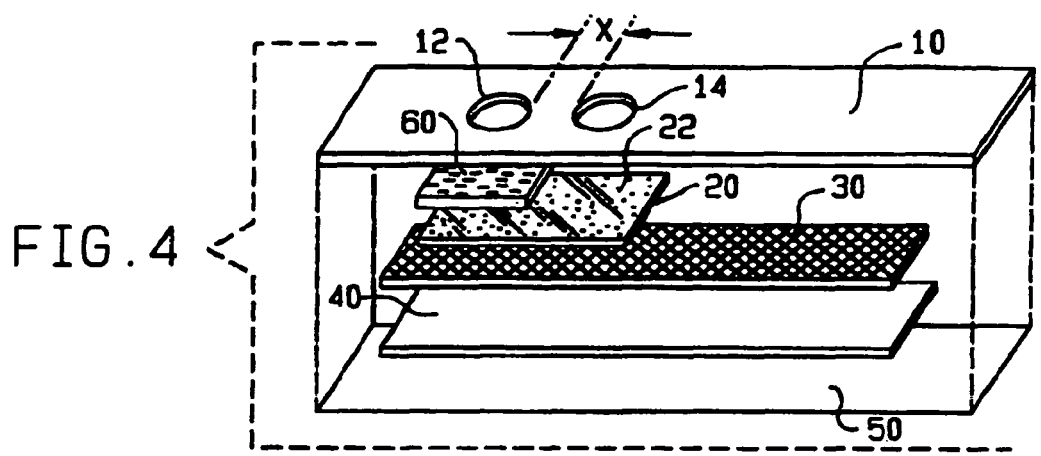

The assay plates useful for the methods and kits of this invention optionally also comprise a substrate (60), such as a glass membrane, containing PF4-complexed particles and other reagents necessary to promote the aggregation reaction. Such a substrate is to be employed where the sample is to be applied directly into the filter well, rather than pre-mixed with a solution containing the receptor-bearing particles. The substrate should be positioned between the top member and the filter means and should extend across the filter well, as shown in FIG. 4.

Figure 5:
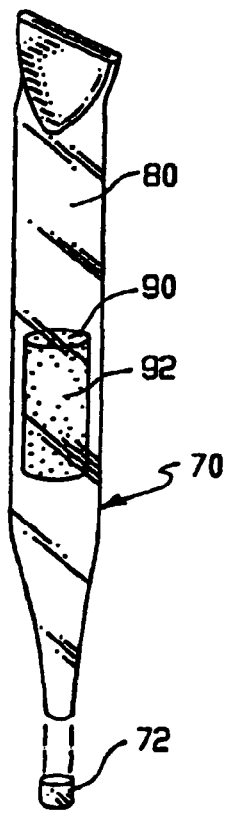
Figure 6:
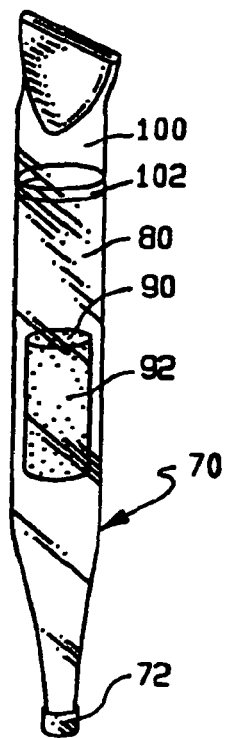
Figure 7:
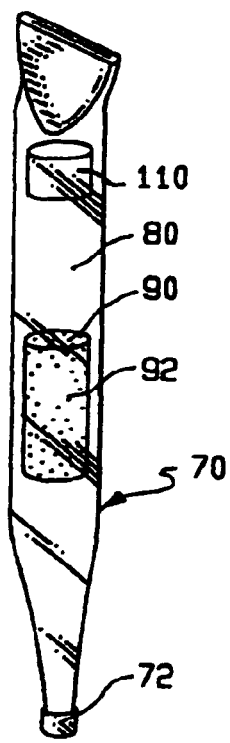

A preferred type of reaction cell (70) is depicted in FIG. 5. One element of reaction cells according to this invention is a container (80) in which PF4-complexed particles may be contacted with a sample suspected to contain a ligand. Such containers may have a variety of shapes. However, a preferably-shaped container is a pipette, such as shown in FIG. 5. It will be appreciated that containers having an open end preferably further comprise a cap (72) for containing the sample and PF4-complexed particles. Preferred containers are disposable and comprise any of the relatively inexpensive, substantially transparent synthetic polymers known in the art. Suitable transparent pipette-shaped containers are available from Franklin, Inc. (Franklin, N.J.).

Within preferred reaction cells are breakable vessels (90) containing the receptor-bearing particles (92). The breakable vessel may comprise glass or some synthetic polymer, so long as the material employed has sufficient structural integrity to contain the particles securely until the particles are to be contacted with the sample, at which time the vessel is broken or ruptured by applied force. Where a reaction cell contains a breakable vessel, it is necessary that the container comprise a relatively supple material through which such rupturing force may be applied to the breakable vessel.

Preferred reaction cells further comprise a kill solution. It is intended that the term "kill solution" denote any solution having the capacity to biologically inactivate any infectious agents in the patient samples employed in performing the assay. Solutions comprising ethanol, formaldehyde, glutaraldehyde, iodophors, or oxidizing bleaches provide examples of kill solutions according to this invention. It is preferred that kill solutions comprise an oxidizing bleach such as sodium hypochlorite. The kill solution is preferably contained in a compartment (100) at one end of the container and separated therefrom by a rupturable membrane (102). Alternatively, the kill solution is contained in a breakable vessel (110) located within the container. The membrane or vessel comprises a material which has sufficient structural integrity to contain the kill solution securely until broken or ruptured by applied force. The kill solution is then released and contacted with any biologically active substances located in the container or on the assay plate, usually upon the completion of an assay.

Figure 8:
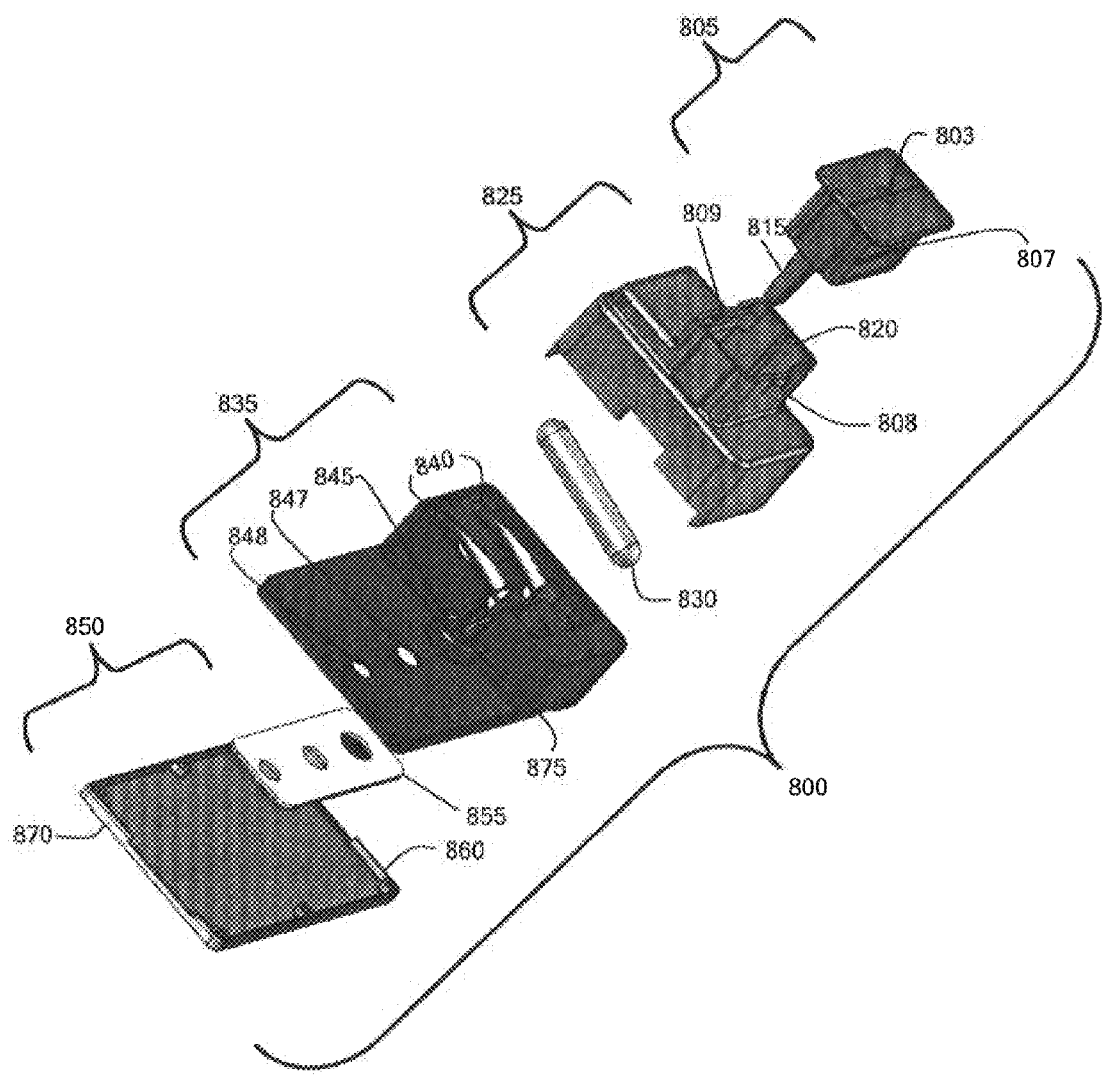
FIG. 8 is an exploded view of an assembly suitable for performing an assay in accordance with the present invention.
Figure 9:
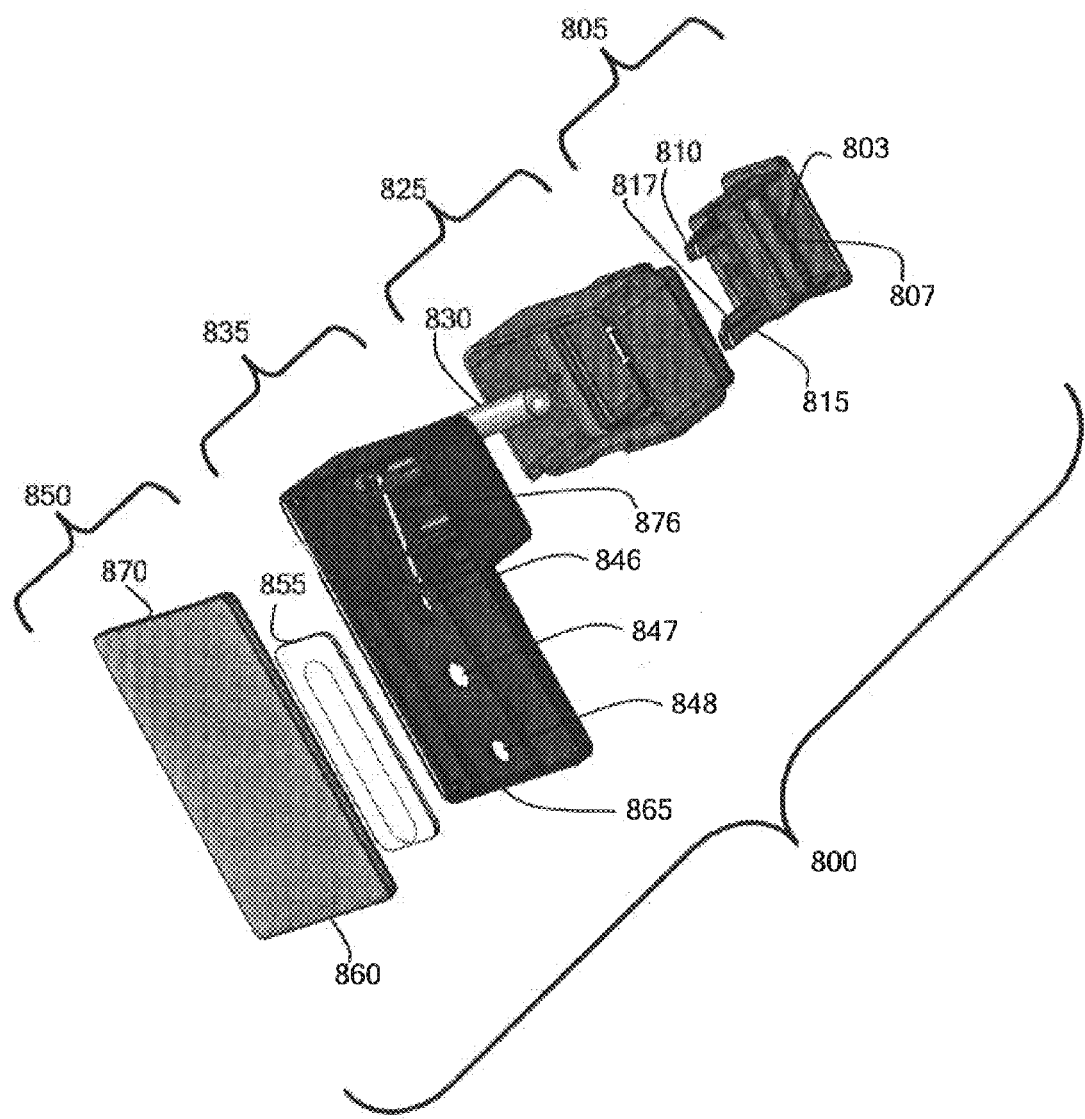
FIG. 9 is a second exploded view of an assembly suitable for performing an assay in accordance with the present invention.

A preferred embodiment of an apparatus for detecting heparin/platelet factor 4 antibodies in a fluid sample is shown in exploded views in FIGS. 8 and 9. Apparatus 800 comprises front side 870 and a tower 805 comprising a sample well 803, latches 807 on two sides, foot 810, and block channel foot 815. Tower 805 engages into opening 820 in cover 825 such that foot 810 crushes ampoule 830 placed in slot 840 in ampoule support 835. Although FIGS. 8 and 9 only show slot 840 with spaces for containing two ampoules 830, more than two ampoules can be used in the apparatus 800 and additional feet may be included in tower 805. The cover 825 also has latches 808 inside such that when tower 805 is depressed, the latches 807 of tower 805 engages with the latches 808 of the cover 825 such that the tower 805 can only be raised to the position 809. Block channel foot 815 of tower 805 blocks the flow of fluid to reagent well 845 in ampoule support 835 following crushing of ampoule 830 by foot 810 of tower 805 when tower 805 is engaged with and pressed into opening 820 in cover 825. Cover 825 is placed over ampoule support 835.

Preferably, cover 825 and ampoule support 835 can snap together with bottom plate 850 holding test strip 855 in place. Test strip 855, which contains a particulate immunofiltration assay as described above, has a test window 847 and a control window 848, and is held in place by indentation 865. In alternative embodiments, different structures may be employed to hold and orient test strip 855. Test strip 855 receives one or more reagents from reagent well 845 via channel 875, typically when reagent is released from ampoule 830 by depressing tower 805 and then withdrawing it to position 809 to unblock channel 875 blocked by block channel foot 815 of tower 805. Preferably, the reagent comprises particles complexed to platelet factor 4 (PF4). Tower 805 further comprises spur 817 for crushing another ampoule to allow mixing two (or more) reagents prior to their flowing to reagent well 845. In alternative embodiments, spur 817 may not be adjacent to block channel foot 815.

FIG. 9 shows reagent well underside 846 and channel underside 876. As shown by FIGS. 8 and 9, the indentations guide and preferably engage different parts such that bottom plate 860, test strip 855, ampoule support 835, and cover 825 are engaged to form test device 800 operable by depressing and withdrawing tower 805.

In one embodiment, the apparatus 800 is used in the following manner:

First, the tower 805 is pushed all the way down to engage into opening 820 in cover 825. Second, a patient sample is injected into the sample well 803 of the tower 805. Third, the apparatus 800 is shook side to side along the longitudinal axis of the test strip 855 for five seconds. Fourth, the apparatus 800 is rested on a flat surface for one minute when the patient sample and reagent(s) in the ampoule(s) will form a mixture in the channel 875. Preferably, the reagent comprises particles complexed to platelet factor 4 (PF4). Fifth, the tower 805 is pulled up to a stop position 809 and the apparatus 800 is tilted forward at a forty-five degrees angle and lightly tapped on the side opposing front side 870 such that the mixture will flow into the reagent well 845 where it undergoes reaction in a particulate immunofiltration assay as described above. Finally, the apparatus 800 is laid flat again and rested for ten minutes or until a color is observed in the control window 848.

In certain other embodiments, the kit comprises two components: a container, such as a plastic pipette, containing the reagents. The reagents are contained in crushable ampoules sealed inside the pipette and comprise PF4-coated particles and other agents helpful to promote rapid antigen/antibody binding.

In one embodiment, the reaction cell comprises a breakable vessel that contains PF4-complexed particles. Optionally, the reaction cell comprises a solution that enhances the aggregation reaction. Optionally, the reaction cell comprises a solution that biologically inactivates any infectious agents in the sample.

The reaction cells can be used for mixing and/or incubating a sample with PF4-complexed particles.

Additional objects, advantages, and novel features of this invention will become apparent to those skilled in the art upon examination of the following examples thereof, which are not intended to be limiting, wherein parts and percents are by weight to volume unless otherwise indicated.

EXAMPLES 6.1 HealthTEST™ Heparin/Platelet Factor 4 Antibody Assay

The HealthTEST™ Heparin/Platelet Factor 4 Antibody Assay (Akers Biosciences, Inc.) is a qualitative in vitro diagnostic device, based on PIFA® technology, designed for the detection of heparin/platelet factor 4 antibodies. The device is supplied in a kit comprising a MiniReactor device containing a membrane filtration system and a results window, and a push button reagent dispensing system containing microparticle-based reaction reagents.

The MiniReactor contains a reaction well that allows the sample to react with the reagents. The sample is added to the reaction wall followed by the reagents contained in the reagents dispenser. The reagents contain microparticles coated with isolated or purified PF4 protein as well as additional enhancing agents (e.g., polyethylene glycol 8000 and dextran 10,000 MW) designed to promote rapid aggregate formation of the particles in the presence of specific antibodies in the test sample.

Once the reagents have reacted with the sample in the reaction well, the reaction mixture automatically collects over the membrane filtration system. This system acts to filter aggregated particles, while allowing non-aggregated particles to pass through. Thus, an aggregated, reactive sample will be trapped within the membrane. Since the dyed particles are trapped on this filter, no particles and hence no color, are able to migrate past the positive/negative line on the results window. Conversely, a non-aggregated, non-reactive sample will pass through the membrane filter and into the wicking layers, and color will migrate past the positive/negative line.

The test is a rapid manual assay and can be easily performed when immediate results are required. The test determines the presence of heparin/platelet factor 4 antibodies in serum or plasma through a visual determination of color in a disposable test device. The assay takes less than 5 minutes to perform with a minimal number of steps.

Dyed microparticles coated with heparin/platelet factor 4 antigen provide the visual signal for the results of the assay. The ability of aggregated or non-aggregated particles to move through a filter medium is the measure of the reactivity/non-reactivity of the test sample.

6.1.1 Materials and Methods

Two studies were performed to evaluate the performance of the HealthTEST™ Heparin/Platelet Factor 4 Antibody Assay compared to commercially available standard laboratory methods using fresh samples originating from field sources.

These studies measured the specificity and sensitivity of the test. The results of the comparison studies are summarized in Section 6.1.2.

6.1.2 Results

| Specificity and Sensitivity | | | |
|---|---|---|---|
| | | ELISA | |
| | | Positive | Negative |
| Study #1 Plasma | | | |
| HealthTEST ™ | Positive | 21 | 15 |
| | Negative | 2 | 137 |
| | | 23 | 152 |

Specificity = 90.1% (or 137/152)
Sensitivity = 91.3% (or 21/23)
Overall Agreement = 90.3% (or 158/173)

| Study #2 Serum | | | |
|---|---|---|---|
| HealthTEST ™ | Positive | 21 | 3 |
| | Negative | 2 | 153 |
| | | 23 | 156 |

Specificity = 98.1% (or 153/156)
Sensitivity = 91.3% (or 21/23)
Overall Agreement = 97.2%% (or 174/179)

Reproducibility

A study, which measured the reproducibility of the test, was performed using 5 replicates each of positive and negative patient controls which were tested with the HealthTEST™ Heparin/Platelet Factor 4 Antibody Assay daily for 4 consecutive days.

The results show the test is 100% reproducible for both serum and plasma.

6.1.3 Discussion

The HealthTEST™ Heparin/Platelet Factor 4 Antibody Assay is designed to identify patients at risk for developing heparin-induced thrombocytopenia (HIT), a severe allergic-like side effect associated with the use of the anticoagulant heparin. The presence of heparin/platelet factor 4 antibodies is associated with patients at risk for HIT, and is rapidly becoming a standard of care in hematology and cardiology. The determination of the presence of heparin/platelet factor 4 antibodies may therefore contribute significantly in the risk assessment of vascular access thrombosis. The test is intended for use, preferably in a health care facility such as a hospital, where heparin is administered during surgical and other medical procedures. The test was evaluated for performance characteristics in comprehensive studies. These studies have demonstrated that the test is safe and effective for intended use.

Also, these studies show that the HealthTEST™m Heparin/Platelet Factor 4 Antibody Assay is as sensitive and specific as current laboratory procedures, such as enzyme immunoassays (ELISA), yet do not require instrumentation and can be performed in as little as 5 min. These advantages will enable the rapid diagnostic assay system to take advantage of market forces and trends shaping the alternate-site healthcare industry.

EQUIVALENTS

The present invention is not to be limited in scope by the specific embodiments described which are intended as single illustrations of individual aspects of the invention, and functionally equivalent methods and components are within the scope of the invention. Indeed, various modifications of the invention, in addition to those shown and described herein, will become apparent to those skilled in the art from the foregoing description and accompanying drawings using no more than routine experimentation. Such modifications and equivalents are intended to fall within the scope of the appended claims.

All publications, patents and patent applications mentioned in this specification are herein incorporated by reference into the specification to the same extent as if each individual publication, patent or patent application was specifically and individually indicated to be incorporated herein by reference.

Citation or discussion of a reference herein shall not be construed as an admission that such is prior art to the present invention.

I claim:

1. A method for diagnosing heparin-induced thrombocytopenia (HIT) in a human subject suspected of having HIT, the method comprising:
   (a) incubating a liquid sample from the subject in a reaction cell adapted to receive the liquid sample to obtain a reaction mixture, the liquid sample comprising at least one of plasma and serum, and the reaction cell comprising particles complexed to platelet factor 4 (PF4) by adsorption of PF4 directly to the surface of the particles, wherein the particle-complexed PF4 reacts specifically with heparin/platelet factor 4 antibodies in the liquid sample forming specific aggregates in the reaction mixture;
   (b) applying the reaction mixture obtained in step (a) to a filter well of an assay plate, the assay plate comprising:
      (i) a top member having the filter well and an observation well at a fixed distance from the filter well, the filter well being adapted to receive the reaction mixture;
      (ii) a filter means adjacent the top member and extending across the filter well for effecting a first separation of the specific aggregates from non-specifically aggregated particles and unaggregated particles in the reaction mixture such that the non-specifically aggregated and unaggregated particles migrate vertically through the filter means;
      (iii) a wicking means adjacent and in fluid communication with the filter means and extending the length of the filter well and the observation well, the wicking means consisting essentially of a plurality of fibers for effecting a second separation of the specific aggregates that passed through the filter means from the non-specifically aggregated and unaggregated particles that passed through the filter means, the unaggregated particles migrate horizontally through the wicking means at a rate faster than the specific aggregates do, and the unaggregated particles are directly visually detectable through the observation well; and
      (iv) a bottom member adjacent the wicking means; and
   (c) detecting a presence or absence of the unaggregated particles in the observation well,
   wherein the detection of the absence of the unaggregated particles in the observation well indicates the presence of the heparin/platelet factor 4 antibodies in the subject, thereby diagnosing HIT in the subject.

2. The method according to claim 1, wherein the particles have a visually recognizable color which can be ascertained by the unaided eye.

3. The method according to claim 1, wherein the particles are spherical and have a mean diameter from about 0.1 micrometers to about 1.0 micrometers.

4. The method according to claim 1, wherein the particles are anionic.

5. The method according to claim 1, wherein the particles comprise polystyrene.

6. The method according to claim 1, wherein the particles comprise latex.

7. The method according to claim 1, wherein the particles are stabilized with a colloidal stabilizer comprising at least one selected from the group consisting of sodium tripolyphosphate, an anionic detergent, and a nonionic detergent.

8. The method according to claim 1, wherein the filter means comprises a controlled pore membrane having a pore size of about 1 micrometer to about 5 micrometers.

9. The method according to claim 1, wherein the wicking means comprises non-woven fibers of glass or synthetic polymeric material.

10. The method according to claim 1, wherein the reaction cell further comprises a reaction enhancer solution having a pH of 7.2 and comprising a salt in a range from about 0.1% w/v to 1% w/v.

11. The method according to claim 10, wherein the reaction enhancer solution further comprises polyethylene glycol 8000.

12. The method according to claim 10, wherein the reaction enhancer solution further comprises glycine in the range of from about 0.01 molar to about 0.2 molar.

13. The method according to claim 1, wherein the sample comprising heparin/platelet factor 4 antibodies is incubated with the particle-complexed PF4 in the reaction cell for about 30 seconds to about 5 minutes.

14. A method for diagnosing heparin-induced thrombocytopenia (HIT) in a human subject suspected of having HIT, the method comprising:
   (a) incubating a liquid sample from the subject in a reaction cell adapted to receive the liquid sample to obtain a reaction mixture, the liquid sample comprising at least one of plasma and serum, and the reaction cell comprising:

(i) particles complexed to platelet factor 4 (PF4) by adsorption of PF4 directly to the surface of the particles, the particles being stabilized with a colloidal stabilizer comprising at least one selected from the group consisting of sodium tripolyphosphate, an anionic detergent, and a nonionic detergent, wherein the particle-complexed PF4 reacts specifically with heparin/platelet factor 4 antibodies in the liquid sample forming specific aggregates in the reaction mixture; and (ii) a reaction enhancer solution having a pH of 7.2 and comprising a salt in a range from about 0.1% w/v to 1% w/v;

(b) applying the reaction mixture obtained in step (a) to a filter well of an assay plate, the assay plate comprising:

(i) a top member having the filter well and an observation well at a fixed distance from the filter well, the filter well being adapted to receive the reaction mixture;

(ii) a filter means adjacent the top member and extending across the filter well for effecting a first separation of the specific aggregates from non-specifically aggregated particles and unaggregated particles in the reaction mixture such that the non-specifically aggregated and unaggregated particles migrate vertically through the filter means, wherein the filter means comprises a controlled pore membrane having a pore size of about 1 micrometer to about 5 micrometers;

(iii) a wicking means adjacent and in fluid communication with the filter means and extending the length of the filter well and the observation well, the wicking means consisting essentially of a plurality of fibers for effecting a second separation of the specific aggregates that passed through the filter means from the non-specifically aggregated and unaggregated particles that passed through the filter means, the unaggregated particles migrate horizontally through the wicking means at a rate faster than the specific aggregates do, and the unaggregated particles are directly visually detectable through the observation well; and (iv) a bottom member adjacent the wicking means; and (c) detecting a presence or absence of the unaggregated particles in the observation well, wherein the detection of the absence of the unaggregated particles in the observation well indicates the presence of the heparin/platelet factor 4 antibodies in the subject, thereby diagnosing HIT in the subject.

15. The method according to claim 14, wherein the sample comprising heparin/platelet factor 4 antibodies is incubated with the particle-complexed PF4 in the reaction cell for about 30 seconds to about 5 minutes.

* * * * *